US007015636B2

(12) United States Patent
Bolta

(10) Patent No.: US 7,015,636 B2
(45) Date of Patent: Mar. 21, 2006

(54) BALANCED BLUE SPECTRUM THERAPY LIGHTING

(76) Inventor: Charles Bolta, 625 Mathews St., Ft. Collins, CO (US) 80524

( * ) Notice: Subject to any disclaimer, the term of this patent is extended or adjusted under 35 U.S.C. 154(b) by 185 days.

(21) Appl. No.: 10/688,009

(22) Filed: Oct. 17, 2003

(65) Prior Publication Data

US 2004/0093045 A1    May 13, 2004

Related U.S. Application Data

(60) Provisional application No. 60/420,624, filed on Oct. 23, 2002.

(51) Int. Cl.
*H01J 1/62* (2006.01)

(52) U.S. Cl. ...................... 313/487; 313/485

(58) Field of Classification Search ........ 313/483–487, 313/498, 503, 506; 252/301.33
See application file for complete search history.

(56) References Cited

U.S. PATENT DOCUMENTS

2002/0080501 A1 *  6/2002  Kawae et al. ............... 359/799

* cited by examiner

*Primary Examiner*—Vip Patel
(74) *Attorney, Agent, or Firm*—Emery L. Tracy

(57) ABSTRACT

A balanced blue spectrum therapy lighting fixture is provided. The lighting fixture comprises a light source and a mixture of blue light and white light within the light source having a range between approximately 90% 420–490 nm blue light and approximately 10% white light to approximately 10% 420–490 nm blue light and approximately 90% white light.

13 Claims, 3 Drawing Sheets

50/50 Blue/White PL-13 Fluorescent Bulb

Balanced Blue Spectrum Therapy Lighting

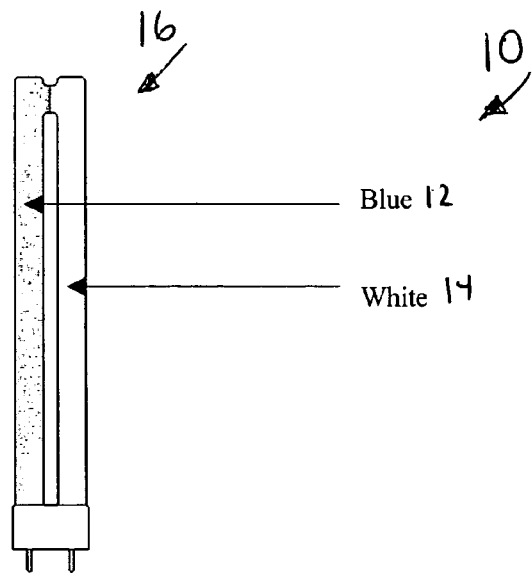
FIG. 1 – 50/50 Blue/White PL-13 Fluorescent Bulb
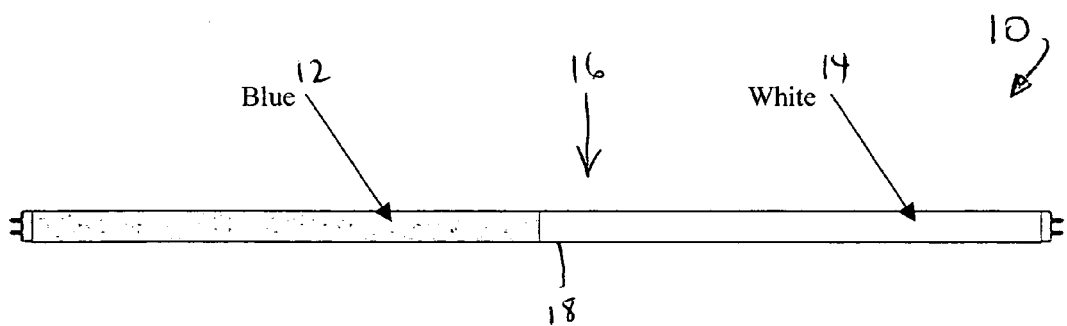
FIG. 3 – 50/50 Blue/White Fluorescent Tube

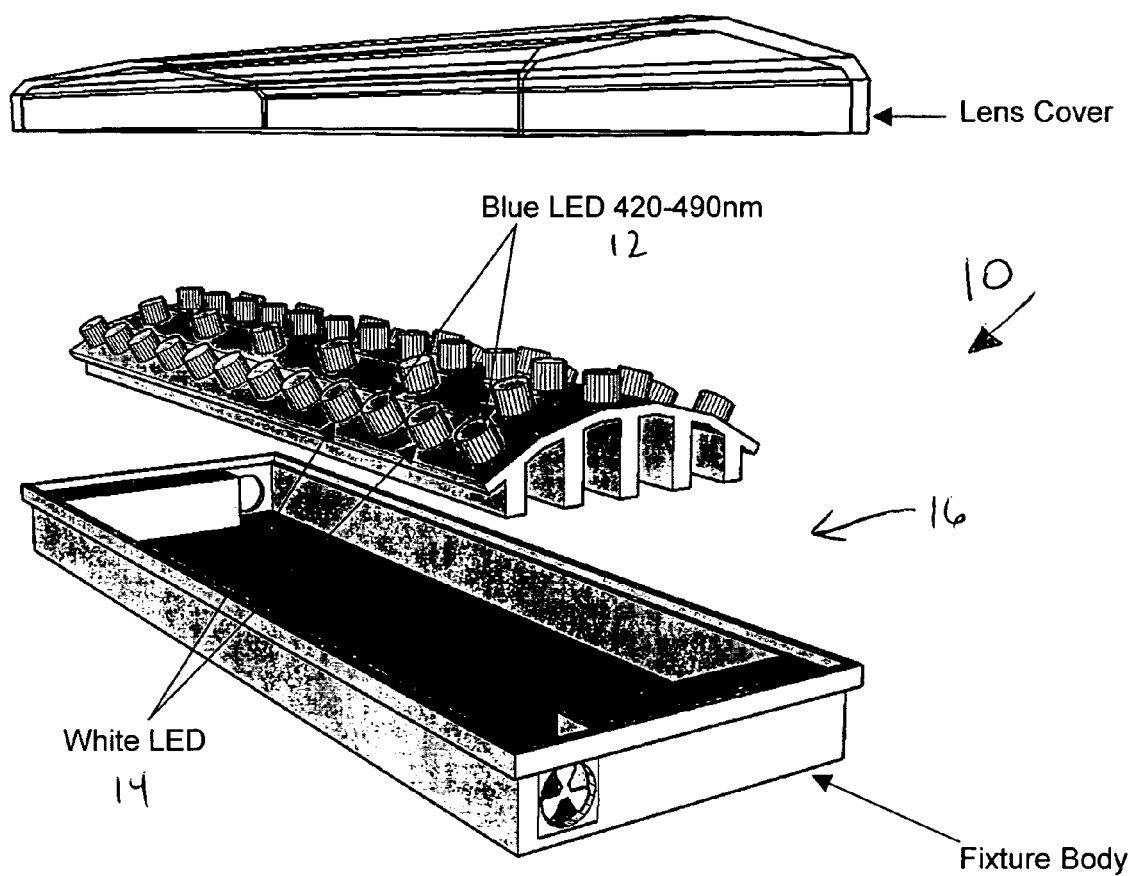
FIG. 2 – Balanced Blue Spectrum Therapy Lighting

1. Alon C
2. After-glow phosphor 20
3. Alon C
4. Scotopic phosphor
5. Alon C

BALANCED BLUE SPECTRUM THERAPY LIGHTING

The present application is a continuation of provisional patent application Ser. No. 60/420,624, filed on Oct. 23, 2002, now abandoned, entitled "Balanced Blue Spectrum Therapy Lighting".

BACKGROUND OF THE INVENTION

1. Field of the Invention

This invention relates generally to therapy lighting and, more particularly, the invention relates to balanced blue spectrum therapy lighting for regulating melatonin.

2. Description of the Prior Art

Although receptive field sizes account for some of the differences in visual sensitivity across the retina, the sensitivity at a given retinal location can also vary. The human eye can process information over an enormous range of luminance (about twelve (12) log units). The visual system changes its sensitivity to light; a process called adaptation, so that it may detect the faintest signal on a dark night and yet not be overloaded by the high brightness of a summer beach scene. Adaptation involves four major processes:

1. Changes in Pupil Size. The iris constricts and dilates in response to increased and decreased levels of retinal illumination. Iris constriction has a shorter latency and is faster (about 0.3 s) than dilation (about 1.5 s). There are wide variations in pupil sizes among individuals and for a particular individual at different times. Thus, for a given luminous stimulus, some uncertainty is associated with an individual's pupil size unless it is measured. In general, however, the range in pupil diameter for young people may be considered to be from two (2) mm for high levels to eight (8) mm for low levels of retinal illumination. This change in pupil size in response to retinal illumination can only account for a 1.2 log unit change in sensitivity to light. Older people tend to have smaller pupils under comparable conditions.

2. Neural Adaptation. This is a fast (less than one (1 s) second) change in sensitivity produced by synaptic interactions in the visual system. Neural processes account for virtually all the transitory changes in sensitivity of the eye where cone photopigment bleaching has not yet taken place (discussed below)—in other words, at luminance values commonly encountered in electrically lighted environments, below about 600 cd/m². Because neural adaptation is so fast and is operative at moderate light levels, the sensitivity of the visual system is typically well adjusted to the interior scene. Only under special circumstances in interiors, such as glancing out a window or directly at a bright light source before looking back at a task, will the capabilities of rapid neural adaptation be exceeded. Under these conditions, and in situations associated with exteriors, neural adaptation will not be completely able to handle the changes in luminance necessary for efficient visual function.

3. Photochemical Adaptation. The retinal receptors (rods and cones) contain pigments which, upon absorbing light energy, change composition and release ions which provide, after processing, an electrical signal to the brain. There are believed to be four photopigments in the human eye, one in the rods, and one each in the three cone types. When light is absorbed, the pigment breaks down into an unstable aldehyde of vitamin A and a protein (opsin) and gives off energy that generates signals that are relayed to the brain and interpreted as light. In the dark, the pigment is regenerated and is again available to receive light. The sensitivity of the eye to light is largely a function of the percentage of unbleached pigment. Under conditions of steady brightness, the concentration of photopigment is in equilibrium; when the brightness is changed, pigment is either bleached or regenerated to reestablish equilibrium. Because the time required to accomplish the photochemical reactions is a finite, change in the sensitivity lag behind the stimulus changes. The cone system adapts much more rapidly than does the rod system; even after exposure to high levels of brightness, the cones will regain nearly complete sensitivity in ten (10 min) minutes–twelve (12 min) minutes, while the rods will require sixty (60 min) minutes (or longer) to fully dark-adapt.

4. Transient Adaptation. Transient adaptation is a phenomenon associated with reduced visibility after viewing a higher or lower luminance than that of the task. If recovery from transient adaptation is fast (less than one (1 s) second), neural processes are causing the change. If recovery is slow (longer than one (1 s) second), some changes in the photopigments have taken place. Transient adaptation is usually insignificant in interiors, but can be a problem in brightly lighted interiors or exteriors where photopigment bleaching has taken place. The reduced visibility after entering a dark movie theater from the outside on a sunny day is an illustration of this latter effect.

SUMMARY

The present invention is a balanced blue spectrum therapy lighting fixture. The lighting fixture comprises a light source and a mixture of blue light and white light within the light source having a range between approximately 90% 420–490 nm blue light and approximately 10% white light to approximately 10% 420–490 nm blue light and approximately 90% white light.

The present invention further includes a method for creating balanced blue spectrum therapy lighting. The method comprises providing a light source and mixing blue light and white light having a range between approximately 90% 420–490 nm blue light and approximately 10% white light to approximately 10% 420–490 nm blue light and approximately 90% white light.

BRIEF DESCRIPTION OF THE DRAWINGS

FIG. 1 is an elevational view illustrating a fluorescent bulb embodiment of the balanced blue spectrum therapy lighting, constructed in accordance with the present invention;

FIG. 2 is an exploded perspective view illustrating the balanced blue spectrum therapy lighting, constructed in accordance with the present invention;

FIG. 3 is an elevational view illustrating a fluorescent tube embodiment of the balanced blue spectrum therapy lighting, constructed in accordance with the present invention.

DETAILED DESCRIPTION OF THE PREFERRED EMBODIMENTS

Figure 4:
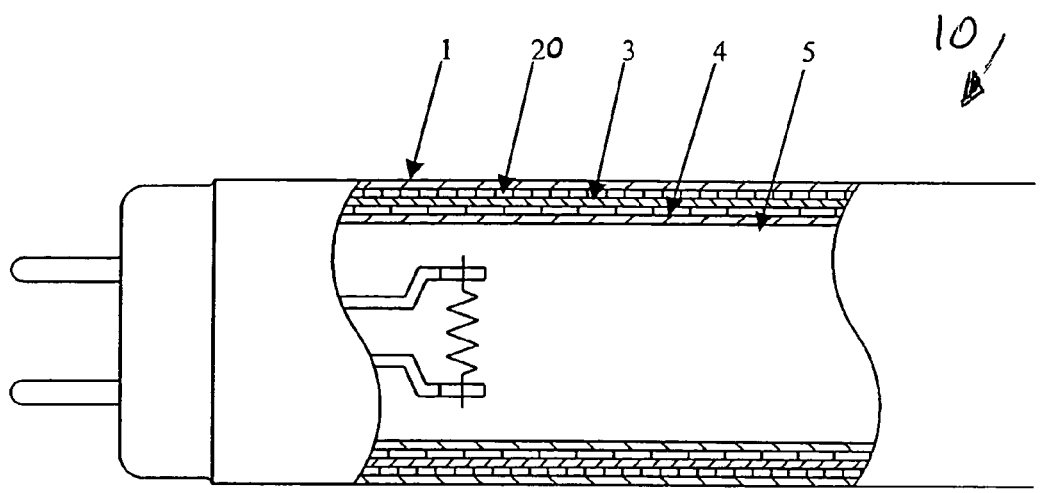
FIG. 4 is sectional view illustrating an embodiment of the balanced blue spectrum therapy lighting, constructed in accordance with the present invention, with an after-glow phosphor undercoat.

As illustrated in FIGS. 1–3, balanced blue spectrum therapy lighting, indicated generally at 10, could be any type of light source that incorporates 420–490 nm blue light 12 with a white light 14. White light 14 is often referred to as cool white, warm white, daylight, or scotopic/photopic light. For this discussion the inventors of the present application define white light 14 as light with a correlated color temperature range of 2,500–10,000 degrees Kelvin and blue light 12 as light with a wavelength range of 420–490 nm.

The benefit of the 420–490 nm blue light 12 is melatonin regulation, but the blue light 12 alone is a light source that may be difficult to work and/or read under. While using this blue light source, if a person looks away, for example, out a window or into another room which is not illuminated by the same blue light source, the surroundings often appear extremely yellow and depth perception may be distorted; this is commonly called visual chaos. Also, in some cases a person's equilibrium may be disturbed. This is because the blue light 12 saturates the rods of the eye and the person's color perception mechanism did not have time to adapt to the consequences of the color spectra of the different light sources, in this case the blue light source and the daylight outside the window. The blue light 12 may be balanced by adding white light, thereby mitigating the negative effects of the blue light 12 while still experiencing the benefits of the blue light melatonin regulation; this is the intention of balanced blue spectrum therapy lighting 10 of the present invention.

As illustrated in FIG. 1, a balanced blue spectrum therapy lighting fixture 16 constructed in accordance with the present invention could contain an array of fluorescent bulbs or L.E.D.'s, some blue 12 and some white 14. For example, a compact fluorescent PL-type bulb, also called a Biax bulb, could have one side emitting blue light 12 and one side emitting white light 14. This would be a single bulb that emits a balanced light. When the bulb is manufactured, first one half of the bulb would be filled with the 420–490 nm blue phosphor and baked, then the other side would be filled with white phosphor and baked. The various amounts of each blue and white would be balanced appropriately for each specific application. The range can go from 90% 420–490 nm blue light 12 and 10% white light 14, to only 10% blue light 12 and 90% white light 14 depending on the application. The preferred ratio is 50% blue light 12 and 50% white light 14.

A balanced blue spectrum therapy lighting fixture 10 constructed in accordance with the present invention can be adjustable with a switching mechanism, either electronic or mechanical, or even activated by radio frequency switching so that a person can adjust the blue and white scotopic/photopic light levels, thereby affecting their melatonin levels as desired.

As illustrated in FIG. 3, color sleeves 18 over a light source could provide balanced blue spectrum therapy lighting 10 as described and claimed herein. The color sleeves 18 could be adjustable depending on the application and the melatonin levels or visual acuity desired.

The balanced blue spectrum therapy lighting 10 of the present invention can be incorporated into fiber optics by making one fiber for blue light 12 and one fiber for white light 14.

As illustrated in FIG. 4, the balanced blue spectrum therapy lighting 10 of the present invention can be combined with an after-glow phosphor undercoat 20 for applications that require emergency lighting.

Example Formula for Preferred Scotopic Phosphor Blend:

| Preferred Approx. % | Phosphor Chemical Composition | Phosphor Peak (nm) |
|---|---|---|
| 40 | $SrO(P_2O_5B_2O_3)$: Eu | 478 |
| 22 | $Y_2O_3$: Eu | 611 |
| 20 | $LaPO_4$: Co, Tb | 544 |
| 18 | $Sr_2P_2O_7$: Eu | 421 |
| 8 | $BaMg_2Al_{16}O_{27}$: Eu | 450 |

Note:
The phosphor peaks (nm) of 421, 450, and 478 in this example are scotopic and fall within the range as referred to melatonin regulates the circadian cycle of sleep.

Note:
This phosphor blend above by itself has biological response to melatonin suppression and could be used for general lighting in any environment.

The preferred scotopic phosphor blend for visual acuity of the balanced blue spectrum therapy lighting 10 of the present invention is composed of combined commercially available phosphors to give light primarily in the 400–620 nm range, with the resulting emitted light spectrum favoring the human eye scotopic-response curve, peaking at approximately 500 nm. As light levels decrease, the human eye responds more to bluer light and less to yellow/red light. As light levels decrease, the human eye also loses transmission of blue light. With age, the eye also loses transmission of blue light and therefore benefits from more blue-light energy. The intent of a scotopic phosphor blend of the present invention is to address both of these conditions with a phosphor that enhances human vision. In addition, the phosphor combination is balanced to produce a good Color Rendering Index (CRI) for photopic vision. Preferably, this number is eighty-five (85) or greater to allow for very good color differentiation; however, a blend containing lower CRI will still provide excellent visualization for tasks such as reading, which require no color sensitivity.

The preferred scotopic phosphor blend for melatonin regulation is particularly rich in the scotopic spectrum (approximately between 420–550 nm) of light. At approximately 420 nm the melatonin reaction starts and at approximately 550 nm the melatonin reaction ends. The benefit of these wavelengths of light (enhanced blue energy) is that it can reduce the output of melatonin in the human body. Melatonin regulates the circadian cycle of sleep. The preferred scotopic phosphor blend of the present invention not only balances out the negative affects of the 420–490 nm blue light spectrum but also contributes to melatonin reduction and can be adjusted as future research dictates. As of now, the range between 420–490 nm shows the greatest results for melatonin regulation. The blend or mixture in the balanced blue spectrum therapy lighting 10 of the present invention is rich in this area with peaks at 478 nm, 450 nm, and 421 nm. The scotopic blue spectrum blended bulbs are intended for installation in work environments such as in a submarine or an engine room of a boat where there is a lack of sunlight and where it is critical that the worker remain awake and alert. Therefore, the worker will have lower melatonin levels and a better chance to remain awake and alert, and also their eyes would be scotopically stimulated and ready to react to emergency low light situations of an afterglow blend. This scotopic phosphor blend could theoretically be used as light therapy for S.A.D. (Seasonal Affective Disorder) and be therapeutic in a low light environment such as a submarine along with its emergency light qualities.

Balanced Blue Spectrum Therapy Lighting 10 of the present invention could be any type of light source that incorporates blue light 12 (light with a wavelength range of 420–490 nm) with a white light 14 (light with a correlated color temperature range of 2,500–10,000 degrees Kelvin). The blue light 12 can be balanced by adding white light 14 thereby mitigating the negative visual and physiological effects of the blue light 12 while still experiencing the benefits of the blue light melatonin regulation; this is the intention of balanced blue spectrum therapy lighting 10 of the present invention.

Visual acuity: The preferred balanced white light phosphor blend of the present invention is composed of combined commercially available phosphors to give light primarily in the 400–620 nm range, with the resulting emitted light spectrum favoring the human eye scotopic-response curve, peaking at about 500 nm. It is further noted that a white light phosphor blend with a peak of 550 nm is also very acceptable. As light levels decrease, the human eye responds more to bluer light (scotopic) and less to yellow/red light (photopic). As light levels decrease, the human eye also loses transmission of blue light. With age, the eye also loses transmission of blue light and therefore benefits from more blue-light energy. The intent of a scotopic phosphor blend is to address both of these conditions with a phosphor that enhances human vision. In addition, the phosphor combination is balanced to produce a good Color Rendering Index (CRI) for photopic vision. Preferably, this number is 85 or greater to allow for very good color differentiation; however, a blend containing lower CRI will still provide excellent visualization for tasks such as reading, which require little color sensitivity.

Correction of negative perception of scotopic light: Conventional scotopic 420–490 nm blue lamps can produce certain problems: they visually distort skin tones and they may cause headaches and nausea. This balanced blue spectrum therapy lighting 10 of the present invention corrects the color to inhibit the common negative response by the public and eliminate the problems associated with conventional blue scotopic lamps.

Kelvin temperature: The Kelvin correlated color temperature in the higher end of the scotopic to photopic ratio spectrum can range between 5,000° K. and 10,000° K. The inventors of the present application have found the correlated color temperature 7,500° K. super daylight range with a 2.47 scotopic to photopic ratio to be nominally rich in scotopic eye response and a superior complimentary match for the 420–490 scotopic blue phosphor. Note: it is critical that the highest scotopic to photopic ratio be obtained. White light with a correlated color temperature between 2,500° K. and 10,000° K. provides a usable balance to the blue light.

Addition of a UV component: The addition of a UV component to create a full spectrum natural light with UVA/B balance can be added or adjusted for different applications without changing the effectiveness of this scotopic blend.

Example Formula for Preferred Scotopic Phosphor Blend:

| Preferred Approx. % | Phosphor Chemical Composition | Phosphor Peak (nm) |
|---|---|---|
| 40 | SrO($P_2O_5B_2O_3$): Eu | 478 |
| 22 | $Y_2O_3$: Eu | 611 |

| Preferred Approx. % | Phosphor Chemical Composition | Phosphor Peak (nm) |
|---|---|---|
| 20 | $LaPO_4$: Co, Tb | 544 |
| 18 | $Sr_2P_2O_7$: Eu | 421 |
| 8 | $BaMg_2Al_{16}O_{27}$: Eu | 450 |

Note:
The phosphor peaks (nm) of 421, 450, and 478 in this example are scotopic and fall within the range as referred to melatonin regulates the circadian cycle of sleep.

Note:
This phosphor blend above by itself has biological response to melatonin suppression and could be used for general lighting in any environment.

Preferred Scotopic Phosphor Blend for Visual Acuity: The preferred scotopic phosphor blend is composed of combined commercially available phosphors to give light primarily in the 400–620 nm range, with the resulting emitted light spectrum favoring the human eye scotopic-response curve, peaking at approximately 500 nm. As light levels decrease, the human eye responds more to bluer light and less to yellow/red light. As light levels decrease, the human eye also loses transmission of blue light. With age, the eye also loses transmission of blue light and therefore benefits from more blue light energy. The intent of a scotopic phosphor blend is to address both of these conditions with a phosphor that enhances human vision. In addition, the phosphor combination is balanced to produce a good Color Rendering Index (CRI) for photopic vision. Preferably, this number is eighty-five (85) or greater to allow for very good color differentiation; however, a blend containing lower CRI will still provide excellent visualization for tasks such as reading, which require no color sensitivity.

Preferred Scotopic Phosphor Blend for Melatonin Regulation: The preferred scotopic phosphor blend for melatonin regulation is particularly rich in the scotopic spectrum (approximately between 420–550 nm) of light. At approximately 420 nm the melatonin reaction starts and at approximately 550 nm the melatonin reaction ends. The benefit of these wavelengths of light (enhanced blue energy) is that it can reduce the output of melatonin in the human body. Melatonin regulates the circadian cycle of sleep. The preferred scotopic phosphor blend of the present invention not only balances out the negative affects of the 420–490 nm blue light spectrum but also contributes to melatonin reduction and can be adjusted as future research dictates. As of now the range between 420–490 nm shows the greatest results for melatonin regulation. The blend of the present application is rich in this area with peaks at 478 nm, 450 nm, and 421 nm. The scotopic blue spectrum blended bulbs are intended for installation in work environments such as in a submarine or an engine room of a boat where there is a lack of sunlight and where it is critical that the worker remain awake and alert. Therefore, the worker will have lower melatonin levels and a better chance to remain awake and alert, and also their eyes would be scotopically stimulated and ready to react to emergency low light situations. This scotopic phosphor blend could theoretically be used as light therapy for S.A.D. (Seasonal Affective Disorder) and be therapeutic in a low light environment such as a submarine along with its emergency light qualities.

Emergency response: Human response time is critical in an emergency. Balanced blue spectrum therapy lighting 10 of the present invention can be combined with an after-glow phosphor undercoat 20. These particular scotopic phosphor blends produce light that enhances the eye's ability to adapt to varying lower light levels, therefore photochemical adaptation and transient adaptation response times are quicker. Because the time required to accomplish photochemical reactions is a finite, change in the sensitivity lag behind the stimulus changes. The cone system adapts much more rapidly than does the rod system; even after exposure to high levels of brightness, the cones will regain nearly complete sensitivity in approximately ten (10 min) minutes to twelve (12 min) minutes, while the rods will require approximately sixty (60 min) minutes (or longer) to fully dark-adapt. These scotopic blends in fact places the eye in a state of emergency readiness because the eye is already operating under higher scotopic light levels therefore engaging the stimulation of the rod receptors in the eye. The amount of scotopic enhancement of these blends that can be adjusted determines the amount of increased or decreased dilation of the pupil and engagement of the eye's rods. The amount of dilation and rod receptor stimulation under this scotopic blend prepares the eye to respond to the lower light levels of the after-glow phosphor blend which is primarily scotopic light and has a low light response curve of approximately 500 nm when the lamp power is turned off. Therefore the eye's photochemical adaptation and transient adaptation response times are quicker. Therefore human response time is critically reduced in an emergency. Scotopic illuminant predicts pupil size and has been demonstrated in several studies. The afterglow light output will continue for a period of time after power is cut off, the bulb is broken, and gasses released; and even the pieces on the floor will continue to emit light, therefore maximizing this emergency lighting bulb to its greatest potential. The bulb, when charged can be removed from the fixture. The bulb will continue to glow and can be used as a portable emergency light source.

Energy efficiency: A lamp containing these scotopic rich phosphor blend needs two-thirds (⅔) the power to achieve the same visual acuity as photopic lighting. Less bulbs use less power, one-third (⅓) less, that way a submarine or boat or military installation can use its electrical resources for offense or defense. These phosphor blends are critical as to application of use of energy in a critical situation such as a submarine or military installation where the amount of bulbs and wattage can be reduced with the use of these scotopic phosphor blends, therefore electrical power can be diverted to more critical uses such as offense or defense. Also, the power can be shut off to the lights and they still have emergency lighting leaving extra power for emergency use. Scotopic light usage and reduction of energy used is well documented. The eye has to work less hard to achieve the same visual acuity. In a submarine, an engine room on a boat, or a building it is critical that power consumption be used for defense or offense rather than for lighting. Therefore the use of scotopic rich light is of great importance. Lamps with combinations of these scotopic blends and after-glow phosphor can be used in remote locations of any building under emergency situations where power is disconnected.

Glare on monitors: One of the side effects of fluorescent or general photopic lighting is glare on monitors such as computers or other instrumentation. The balanced blue spectrum therapy lighting 10 of the present invention reduces glare, increases visual acuity, and increases black and white contrast. The scotopic blend has a lower lumen output therefore reducing glare on the monitor screen. Approximately one-third (⅓) to one-half (½) less lumens as in regular fluorescent lighting are needed for the same visual acuity. Typically L.E.D.'s have a lower lumen output than fluorescent lamps, so L.E.D.'s that operate in the scotopic range would have less glare on monitors. The function of this scotopic blend is to increase the amount of perceived light entering the human eye.

Pilot room on boat or airplane: Side effects of nighttime navigation include the problem of reading under light to see charts or instrumentation and then having to look out into darkness, and also becoming drowsy and falling asleep. This is another example of photochemical adaptation and transient adaptation response times. With the scotopic balanced blue spectrum therapy lighting blend 10 of the present invention, the pilot could read or perform tasks and look out into darkness with minimal effect on his or her visual adaptation, and could also turn the brighter scotopic light off and still have a background blue illumination for moving about the cabin. As an example, the standard procedure when using a periscope on a submarine is to turn off the bright lighting and turn on a photopic red light in order to darken the room. This balanced blue spectrum blend of the present invention would be applicable in this situation where the scotopic light would be the normal operating light and the blue spectrum therapy lighting would function to lower the interior light level when using the periscope. Another option is to modify this scotopic phosphor blend to be in the blue range for a bulb that could replace the photopic red light currently turned on when the periscope is being used. Furthermore, the blue range would be better than the photopic red light and could possibly be used as a primary light source for when the periscope is being used rather than the photopic red that is being used now. This scotopic blue blend would also benefit pilots by regulating melatonin stimulus as discussed. Falling asleep is a well-documented problem for nighttime navigators. In the event of a catastrophic power failure we could add an after-glow phosphor undercoat and their eyes would be ready to see in darkness and the illumination would allow the pilot to continue to read charts or perform simple tasks because the eyes would already have the rods engaged and ready to see in the lower light.

Compact Fluorescent PL-Type Bulb: A compact fluorescent PL-type bulb 16, also called a Biax bulb, could have one side emitting blue light 12 and one side emitting white light 14. This would be a single bulb 16 that emits a balanced light. When the bulb 16 is manufactured, first one half of the bulb 16 would be filled with the 420–490 nm blue phosphor and baked, then the other side would be filled with white phosphor and baked. See FIG. 1.

L.E.D. Application: A blue L.E.D. light may be balanced by adding white LED light. The L.E.D. array can be configured with various amounts of each blue and white L.E.D.'s, balanced appropriately for each specific application. The range can go from 90% 420–490 nm blue L.E.D.'s and 10% white L.E.D.'s, to only 10% blue L.E.D.'s and 90% white L.E.D.'s depending on the application. The L.E.D. Luminaire may be adjustable with a switching mechanism, either electronic or mechanical, or even activated by radio frequency so that a person can adjust the blue and white scotopic/photopic light levels, thereby affecting their melatonin levels as desired. See FIG. 2.

Arrays: A balanced blue spectrum therapy lighting fixture 10 could contain an array of fluorescent bulbs or L.E.D.'s, some blue and some white. The various amounts of each blue and white would be balanced appropriately for each specific application. The range can go from 90% 420–490 nm blue and 10% white, to only 10% blue and 90% white depending on the application. The preferred ratio is 50% blue light 12 and 50% white light 14.

Switching Mechanism: A balanced blue spectrum therapy lighting fixture 16 may be adjustable with a switching mechanism, either electronic or mechanical, or even activated by radio frequency switching so that a person can adjust the blue and white scotopic/photopic light levels, thereby affecting their melatonin or visual acuity levels as desired.

Color Sleeves: Color sleeves 18 and/or transparencies in the range of 420–490 nm blue spectrum over a light source could provide balanced blue spectrum therapy lighting. The color sleeves 18 could be slipped on a fluorescent light and/or any light source including incandescent and adjust the blue to white ratio depending on the application and the melatonin levels desired. See FIG. 3.

Fiber Optics: Balanced blue spectrum therapy lighting can be incorporated into fiber optics by making one fiber for blue light 12 and one fiber for white light 14 in any combination ratio desired.

After-Glow Phosphor Undercoat: The balanced blue spectrum therapy lighting 10 can be combined with an after-glow phosphor undercoat 20 for applications that require emergency lighting. The after-glow phosphor undercoating 20 is put in a fluorescent tube first, under either the blue light phosphor or the white light phosphor or both. When power is cut to the fluorescent bulb the after-glow phosphor blend still continues to emit visual light for emergency situations. See FIG. 4.

Variance of use: There are many types of lamps and fixtures that could incorporate balanced blue spectrum therapy lighting. This balanced blue spectrum blend could be put into a wide variety of fluorescent tubes and bulbs. Incandescent bulbs could be tinted to different ratios, an example being a typical bulb could be tinted one half blue and one half no tint. Another example would be where the whole bulb is tinted blue and it is put in a light fixture with another bulb that's not tinted and the ratio could be adjusted depending on the visual acuity and melatonin regulation desired. These scotopic bulbs could fit into existing fluorescent lighting fixtures for general luminance. These could also be put into any location where predictable low light happens frequently such as in New York City subways.

In sum, the balanced blue spectrum therapy lighting 10 of the present invention could be any type of light source that incorporates 420–490 nm blue light 12 with a white light 14. White light 12 is often referred to as cool white, warm white, daylight, or scotopic/photopic light. In the present application, white light 14 is defined as light with a correlated color temperature range of 2,500–10,000 degrees Kelvin, and blue light 12 is defined as light with a wavelength range of 420–490 nm.

The benefit of the 420–490 nm blue light 12 is melatonin regulation, but the blue light 12 alone is a light source that may be difficult to work and/or read under. While using this blue light source, if a person looks away, for example out a window or into another room which is not illuminated by the same blue light source, the surroundings may appear extremely yellow and depth perception may be distorted; this is commonly called visual chaos. Also, in some cases a person's equilibrium may be disturbed. This is because the blue light 12 saturates the rods of the eye and the person's color perception mechanism did not have time to adapt to the consequences of the color spectra of the different light sources, in this case the blue light source and the daylight outside the window. With the present invention, the blue light 12 can be balanced by adding white light 14, thereby mitigating the negative effects of the blue light 12 while still experiencing the benefits of the blue light melatonin regulation; this is the intention of balanced blue spectrum therapy 10 lighting of the present invention.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A balanced blue spectrum therapy lighting fixture, the lighting fixture comprising:
   a light source; and
   a mixture of blue light and white light within the light source having a range between approximately 90% 420–490 nm blue light and approximately 10% white light to approximately 10% 420–490 nm blue light and approximately 90% white light.

2. The lighting fixture of claim 1 wherein the blue light is 50% 420–490 mn blue light and 50% white light.

3. The lighting fixture of claim 1 and further comprising:
   an array of fluorescent bulbs or L.E.D.'s, the bulbs and L.E.D.'s containing blue light and white light.

4. The lighting fixture of claim 1 and further comprising:
   a single bulb with one side emitting blue light and the other side emitting white light thereby emitting a balanced light.

5. The lighting fixture of claim 5 wherein one half of the bulb is filled with the 420–490 nm blue phosphor and baked and the other side is filled with white phosphor and baked.

6. The lighting fixture of claim 1 and further comprising:
   a switching mechanism for adjusting blue and white scotopic/photopic light levels thereby affecting melatonin levels.

7. The lighting fixture of claim 6 wherein in the switching mechanism is selected from the group consisting of electronic, mechanical, and radio frequency activation switching.

8. The lighting fixture of claim 1 and further comprising:
   at least one color sleeve positioned over a light source for providing the blue light and white light levels.

9. The lighting fixture of claim 8 wherein the color sleeves are adjustable.

10. The lighting fixture of claim 1 wherein the blue light and white light levels are incorporated into fiber optics, one fiber for blue light and one fiber for white light.

11. The lighting fixture of claim 1 wherein the blue light and white light levels are combined with an after-glow phosphor undercoat.

12. The lighting fixture of claim 1 wherein the lighting source contains the following scotopic phosphor blend:

| Approx. % | Phosphor Chemical Composition | Phosphor Peak (nm) |
|---|---|---|
| 40 | $SrO(P_2O_5B_2O_3)$: Eu | 478 |
| 22 | $Y_2O_3$: Eu | 611 |
| 20 | $LaPO_4$: Co, Tb | 544 |
| 18 | $Sr_2P_2O_7$: Eu | 421 |
| 8 | $BaMg_2Al_{16}O_{27}$: Eu | 450. |

13. The lighting fixture of claim 12 wherein the scotopic phosphor blend comprises phosphors to give light primarily in the 400–620 nm range.

* * * * *